US00PP37405P2

(12) United States Plant Patent
Captein

(10) Patent No.: US PP37,405 P2
(45) Date of Patent: May 5, 2026

(54) ***HYDRANGEA* PLANT NAMED 'OLLEDE'**

(50) Latin Name: *Hydrangea paniculata*
Varietal Denomination: OLLEDE

(71) Applicant: Breederplants VOF, Gouda (NL)

(72) Inventor: Antonius M.M. Captein, Alphen aan den Rijn (NL)

(73) Assignee: Breederplants VOF, Gouda (NL)

( * ) Notice: Subject to any disclaimer, the term of this patent is extended or adjusted under 35 U.S.C. 154(b) by 0 days.

(21) Appl. No.: 19/338,930

(22) Filed: Sep. 24, 2025

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan Mccormick Ewoldt
(74) *Attorney, Agent, or Firm* — Weatherly IP Solutions, LLC; Karen P. Bechtold; James M. Weatherly

(57) ABSTRACT

A new *Hydrangea* plant named 'OLLEDE' particularly distinguished by a short plant having early flowering with white inflorescence fading to greyed-red when mature, is disclosed.

4 Drawing Sheets

Genus and species: *Hydrangea paniculata.*
Variety denomination: 'OLLEDE'.

BACKGROUND OF THE NEW PLANT

The present invention comprises a new and distinct variety of *Hydrangea* plant, botanically known as *Hydrangea paniculata*, and hereinafter referred to by the variety name 'OLLEDE'. 'OLLEDE' originated from an open pollination in autumn of 2019 using a female *Hydrangea paniculata* 'Grandiflora' parent (unpatented) and an unknown male parent. Seeds from the open-pollination were selected in July 2021 in Alphen aan den Rijn in the Netherlands.

'OLLEDE' was first propagated in May 2022 in Aphen aan den Rijn in the Netherlands. 'OLLEDE' was found to reproduce true to type in successive generations of asexual propagation via softwood cuttings.

SUMMARY

The following are the most outstanding and distinguishing characteristics of this new variety when grown under normal horticultural practices in Boskoop, The Netherlands.

1. Early flowering;
2. White inflorescence fading to greyed-red when mature; and
3. Short height of the plant.

DESCRIPTION OF THE PHOTOGRAPHS

This new *Hydrangea* plant is illustrated by the accompanying photographs which shows the plant's overall plant habit including form, and foliage. The photographs are of a two-year-old plant from cuttings grown in a 21-cm container. Photos were taken in August 2021 in Boskoop, The Netherlands. The colors shown are as true as can be reasonably obtained by conventional photographic procedures.

DESCRIPTION OF THE NEW VARIETY

Figure 1:
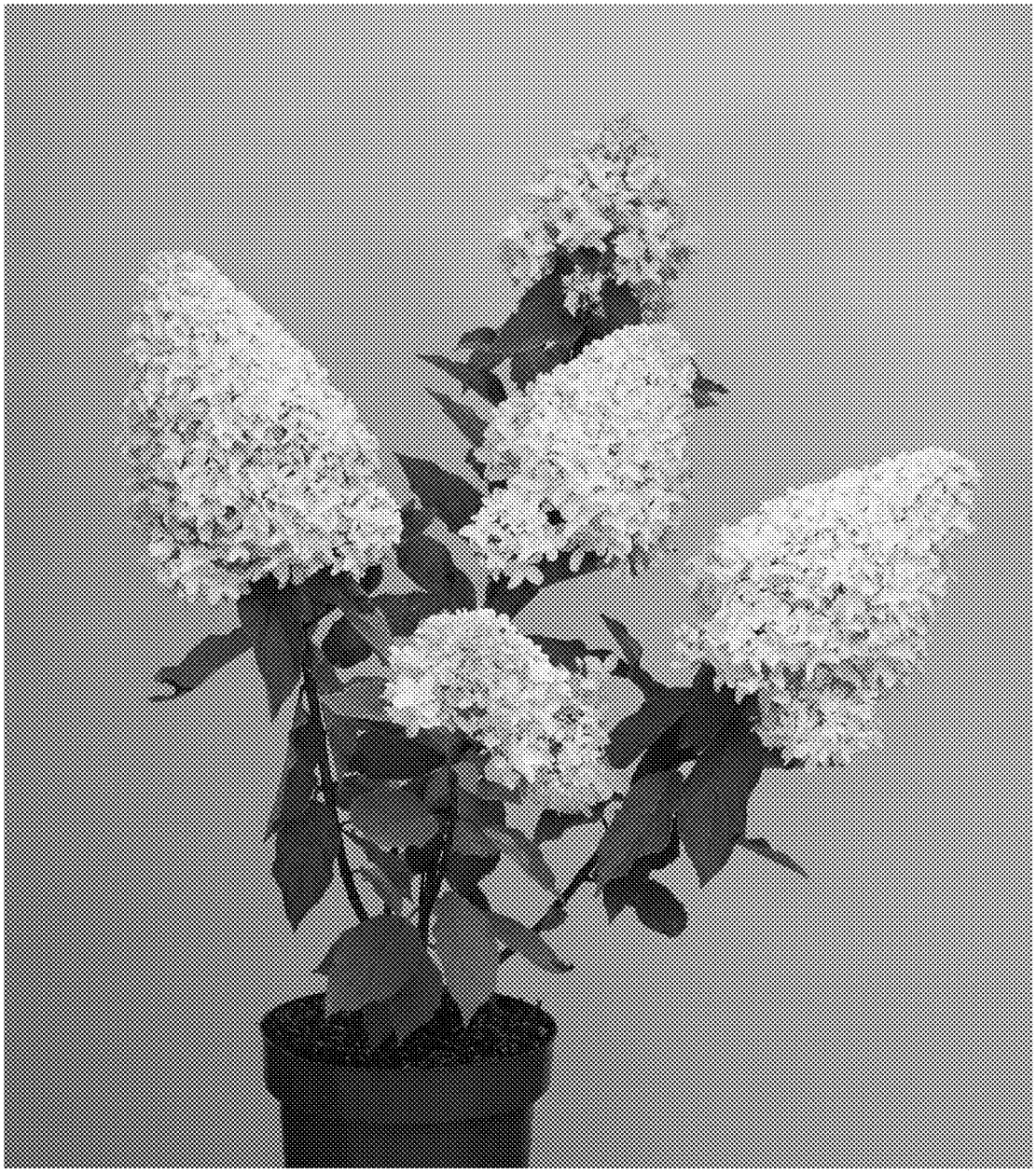
FIG. 1 shows the overall plant habit of 'OLLEDE'.
Figure 2:
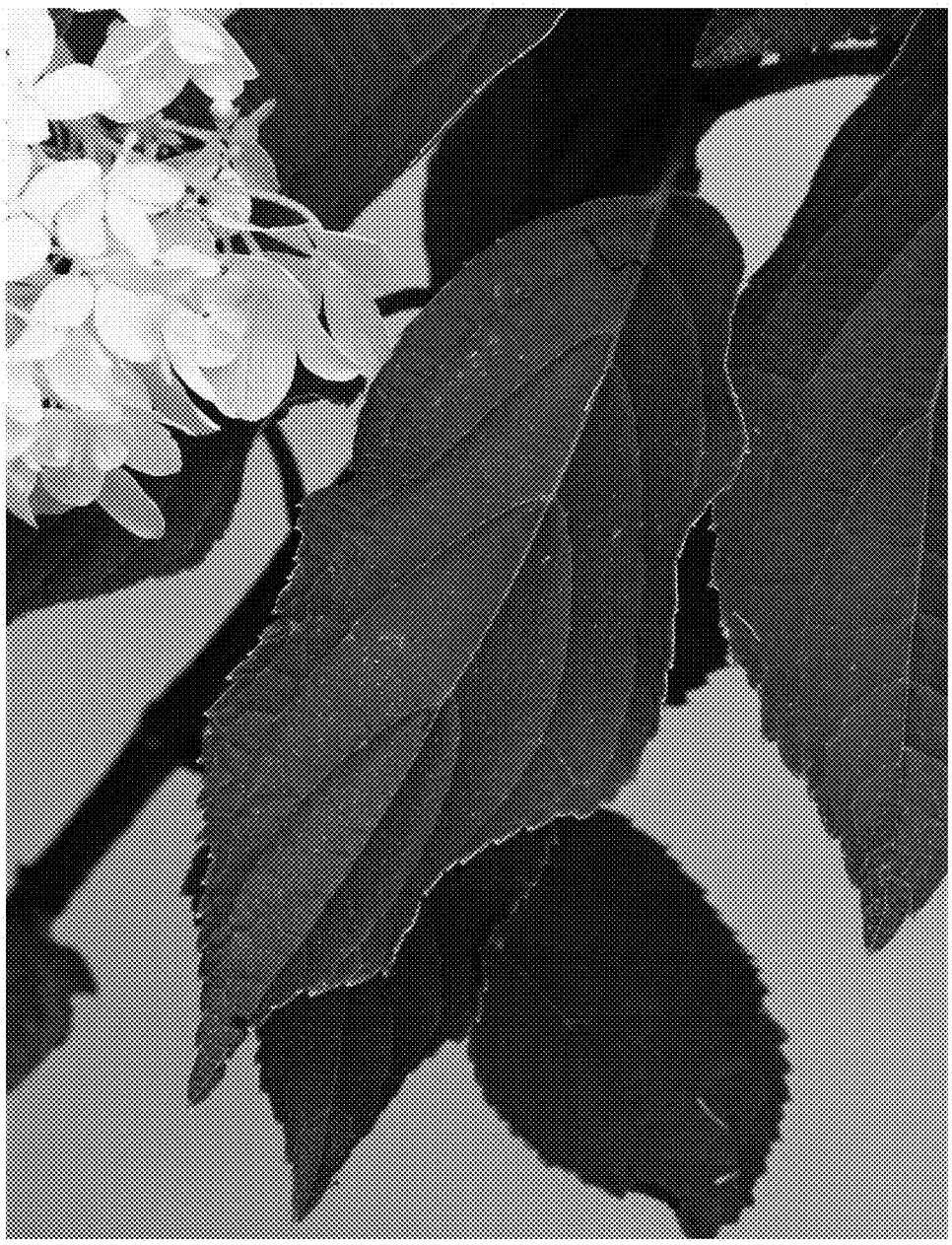
FIG. 2 shows a close-up of the foliage.
Figure 3:
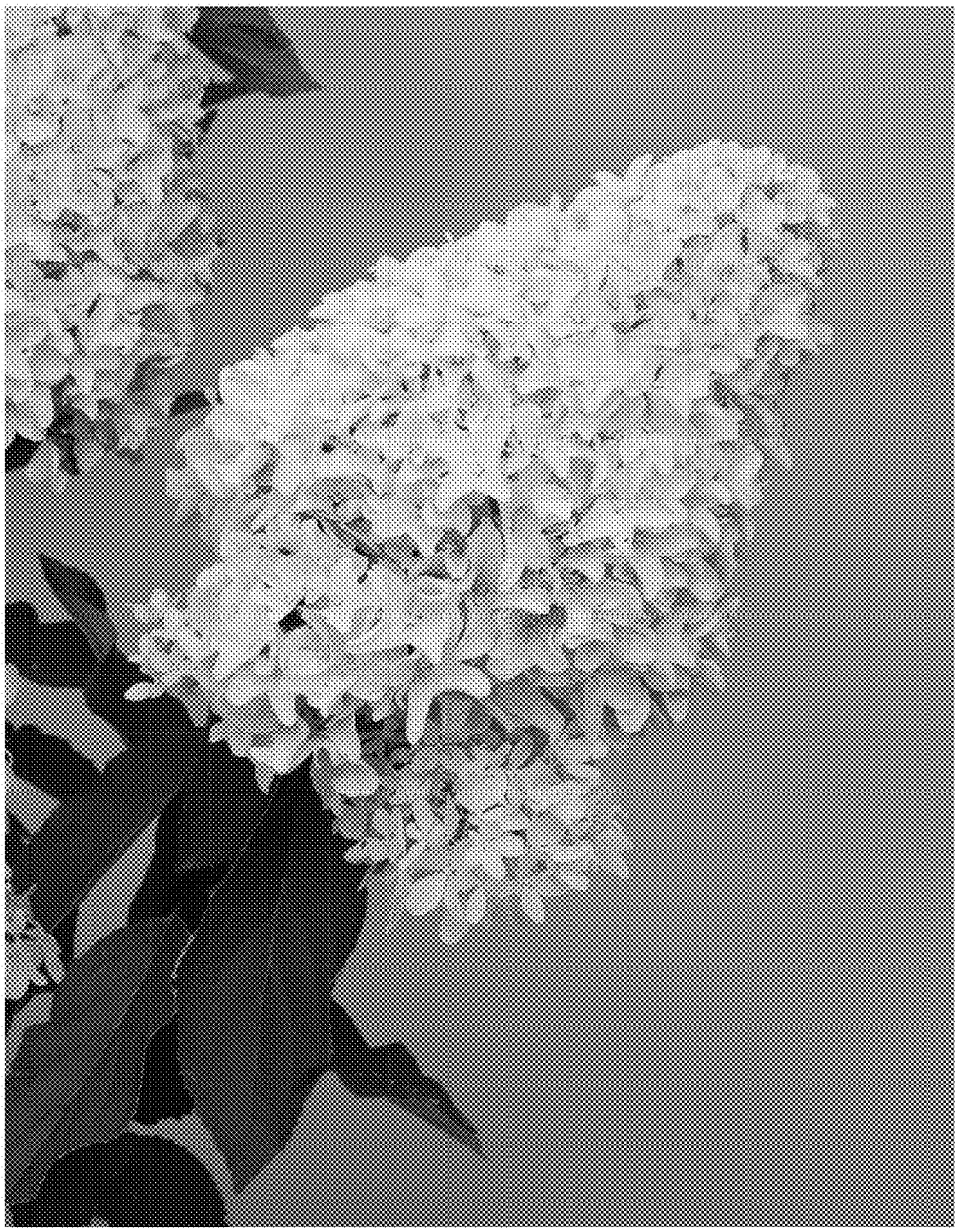
FIG. 3 shows a close-up of the inflorescence with sepals fully open.
Figure 4:
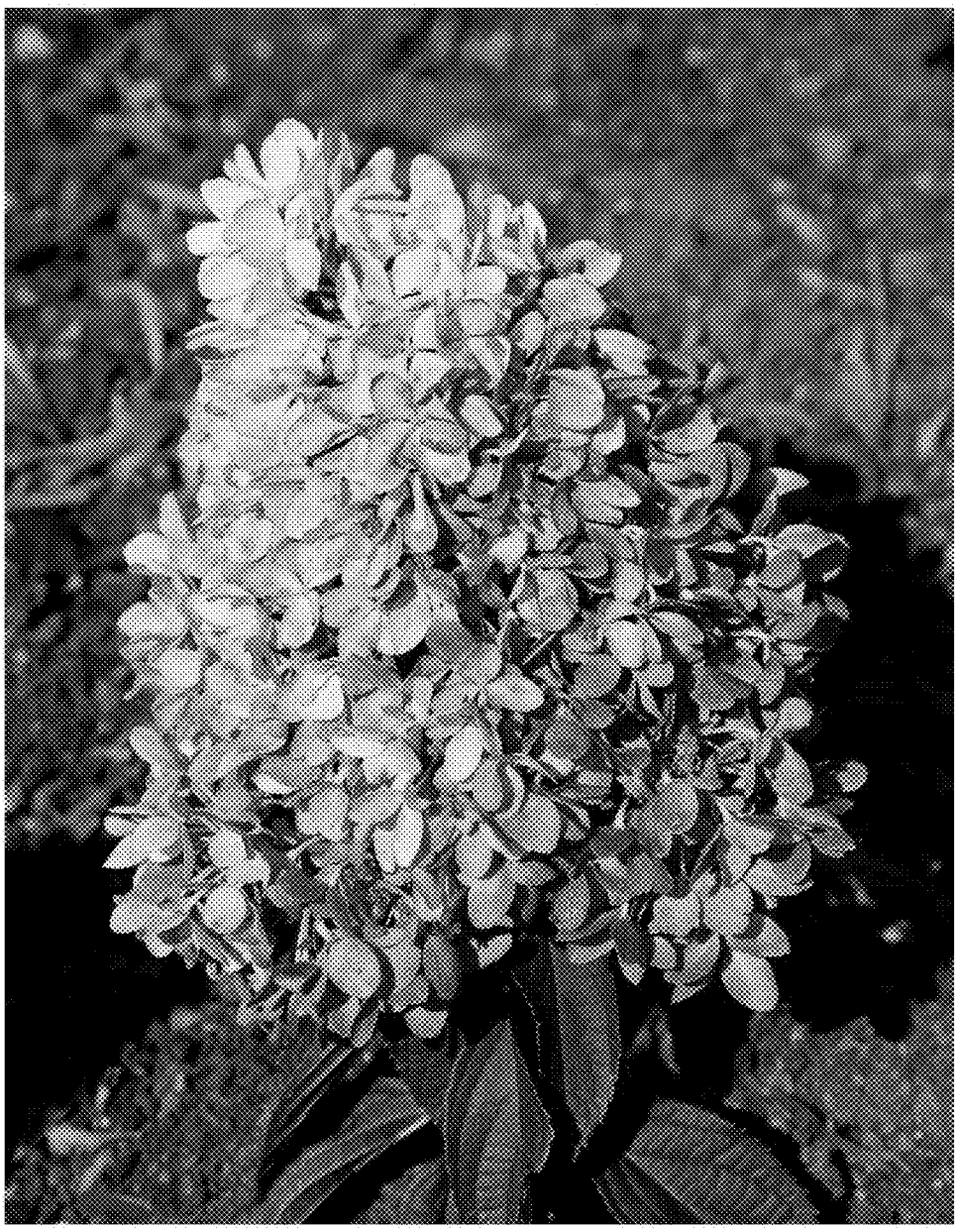
FIG. 4 shows a close-up of the plant's mature inflorescence color with sepals fading.

The following detailed descriptions set forth the distinctive characteristics of 'OLLEDE'. The data which define these characteristics were collected from asexual reproductions carried out in Boskoop, The Netherlands. Data was collected on two-year old plants grown outdoors in 23 cm circular containers in Boskoop, The Netherlands in August 2024. The range of day temperatures was 18° C. to 30° C. and the range of night temperatures was 12° C. to 20° C. Color references are to The R.H.S. Colour Chart of The Royal Horticultural Society of London (R.H.S.), $6^{th}$ edition (2019 reprint).

Classification:

*Family.*—Hydrangeaceae.
*Botanical.—Hydrangea paniculata.*
*Common.—Hydrangea.*
*Designation.*—'OLLEDE'.

Plant:

*Propagation type.*—Softwood.
*Time to produce a finished plant.*—Average 12 months.
*Appropriate for what size of container.*—Field grown and in 23 cm pots.
*Plant shape.*—Broad obovate.
*Average plant height.*—67.5 cm.
*Average plant diameter.*—57.5 cm.
*Growth habit.*—Broad spreading-upright.
*Growth rate.*—Moderate.
*Vigor.*—Moderate.
*Heat tolerance.*—At least tolerant to USDA Zone 9.
*Cold tolerance.*—At least tolerant to USDA Zone 5.
*Tolerance to wind.*—Moderate.
*Tolerance to rain.*—Moderate to high.

Branches:

*Habit*.—Freely branching.

*Basal branching*.—Present.

*Pinching*.—Not required but improves branching.

*Lateral branches*.—Number of lateral branches per plant: 6. Length: Average is 39.6 cm, excluding inflorescence. Diameter: 0.6 cm. Internode length: 4.7 cm. Appearance and shape: Rounded. Aspect/angle: Lateral branches in an average angle of 50° to main branch. Strength: Strong. Color (immature): RHS 146C and RHS 146D (Yellow-green). Color (mature): RHS N199B (Grey-brown); Older bark: RHS N199B, RHS N199C and RHS N200B (Grey-brown and brown). Pubescence: Young stems moderately covered with very short adpressed hairs, average length: 0.5 mm. Lenticels: Quantity, per unit area: stems moderately covered with lenticels. Length: 1.0 mm. Width: 0.75 mm. Color: RHS 165C and RHS 165D (Greyed-orange).

Foliage:

*Arrangement*.—Opposite or in whorls of three.

*Shape*.—Elliptic to elliptic-ovate, flat to slightly carinate.

*Apex*.—Apiculate.

*Base*.—Obtuse to acute.

*Margin*.—Serrate.

*Length*.—11.6 cm.

*Width*.—5.6 cm.

*Texture*.—Upper surface: Smooth, sparsely pubescent (very short adpressed hairs, average length of 0.5 mm), slightly glossy. Lower surface: Smooth, glabrous, main vein and secondary veins moderately pubescent (very short hairs, average length of 0.75 mm), very slightly glossy.

*Venation pattern*.—Pinnate.

*Venation color*.—Upper surface: RHS 156C and RHS 152D (Yellow-green). Lower surface: RHS 193A (Greyed-green) and RHS 183D: fading greyed-purple towards the petiole.

*Color*.—Immature: Upper surface: RHS 143A (Green). Lower surface: RHS 143C (Green). Mature: Upper surface: RHS 137B (Green). Lower surface: RHS 146B (Yellow-green).

*Petiole*.—Length: 2.3 cm. Diameter: 0.2 cm. Color: Upper surface: RHS 184A (Greyed-purple) with main vein RHS 151A (yellow-green). Lower surface: RHS 183D (Greyed-purple). Texture: Upper side: Very slightly glossy, sparsely to moderately covered with very short adpressed hairs, average length: 0.5 mm. Lower side: Very slightly glossy, sparsely covered with very short adpressed hairs, average length: 0.5 mm.

Flowers:

*Natural flowering season*.—Mid-summer to late summer.

*Time to flower*.—One season.

*Fragrance*.—Faint, sweet and pleasant.

*Panicle*.—Shape: Irregular broad conical to near deltoid. Height: 20.2 cm. Diameter: 19.1 cm.

*Peduncle*.—Length: 20.2 cm. Diameter: 0.25 cm. Angle: Main peduncle straight on top of lateral branch (=0°), lateral peduncles in an average angle of 60° to main peduncle. Strength: Moderately strong. Texture: Matte, densely covered with thin adpressed hairs; average length of hairs 0.5 mm. Color: RHS 195B (Greyed-green).

*Sterile florets*.—Bud: Length: 0.8 cm. Diameter: 0.8 cm. Shape: Cup-shaped. Color: RHS 150C (Yellow-green). Florets: Number of sterile flowers per inflorescence: approximately 775. Aspect: Upright and outward to slightly drooping. Shape: Rotate. Diameter: 3.5 cm. Height: 1.6 cm. Lastingness on the plant: Six weeks. Petals: Quantity per flower: Average of 4; occasionally 5. Arrangement: Rotate (cruciform). Shape: Ovate, strongly concave. Apex: Acute. Base: Cuneate. Margin: Entire. Length: 2.0 mm. Width: 1.0 mm. Texture (both surfaces): Smooth, glabrous, slightly glossy. Color: Upper and lower surfaces (when opening): RHS NN155D (White). Upper and lower surfaces (fully opened): RHS NN155D (White). Upper and lower surfaces (mature, fading to): No fading but dropped when mature. Sepals: Quantity per flower: Average of 4; occasionally 5 or 6. Arrangement: Rotate. Shape: Ovate to elliptic, slightly to moderately concave. Apex: Obtuse. Base: Cuneate. Margin: Entire. Length: 2.1 cm. Width: 1.4 cm. Texture (both surfaces): Glabrous and matte. Color: Upper surface (when opening): A blend of RHS 155A and RHS 157C (White to Green-white). Lower surface (when opening): A blend of RHS 155A and RHS 157C (White to Green-white). Upper surface (fully opened): A blend of RHS 155A and RHS 158C (White to yellow-white). Lower surface (fully opened): A blend of RHS 155B and RHS 150D (White to yellow-green). Upper surface (mature, fading to): RHS 145A (Yellow-green), occasionally margined and tipped RHS 180C (Greyed-red). Lower surface (mature, fading to): RHS 184B (Greyed-purple). Pedicel: Length: 1.85 cm. Diameter: 1.0 mm. Angle: Average 40°; varying between 0° and 80°. Strength: Moderately strong. Texture: Matte, very sparsely covered with thin adpressed hairs; average length of hairs: 0.5 mm and shorter. Color: RHS 157B and RHS 157C (Green-white).

*Fertile florets*.—Florets: Quantity per inflorescence: Approximately 500.Aspect: Upright. Shape: Rotate, petals drop when maturing. Diameter: 7.0 mm. Depth (height): 6.0 mm. Flower longevity: Five days. Persistent or self-cleaning: Self-cleaning. Petals: Color: RHS 150C and RHS 150D (Yellow-green). Petals: Petals per flower: Average 5, occasionally 6. Arrangement: Rotate. Shape: Ovate, slightly concave. Tip: Acute. Base: Cuneate. Margin: Entire. Length: 3.0 mm. Width: 1.5 mm. Appearance and texture (both surfaces): Smooth, glabrous, slightly glossy. Color: Upper surface (when opening): RHS NN155D (White). Lower surface (when opening): RHS NN155A (White). Upper surface (fully opened): RHS NN155D (White). Lower surface (fully opened): RHS NN155A (White). Upper surface (mature, fading to): Not fading but dropped when mature. Lower surface (mature, fading to): Not fading but dropped when mature). Sepals: Quantity per flower: 5. Arrangement: Rotate. Shape: Broad Deltoid. Tip: Acute. Base: Broad cuneate. Margin: Entire. Length: 0.75 mm. Width: 1.0 mm. Appearance and texture (both surfaces): Glabrous, matte. Color: Upper surface (when opening): RHS 145B (Yellow-green). Lower surface (when opening): RHS 145B (Yellow-green). Upper surface (fully opened): RHS 145B to RHS 145C (Yellow-green). Lower surface (fully opened): RHS 145B (Yellow-green). Upper surface (mature, fading to): Does not fade. Lower surface (mature, fading to): Does not fade. Pedicel: Length: 3.0 mm (varying between 1.0 mm and 7.0 mm). Diameter: 0.5 mm. Angle: Average 5° (0°=vertical). Strength: Medium. Texture and appearance: Matte, moderately to densely covered with a thin pubescence; average length of hairs: 0.3 mm and shorter. Color: RHS 145C (Yellow-green).

Reproductive organs:

*Sterile flowers*.—Androecium: Present. Number of stamens per flower: 8. Filament length: 3.0 mm. Filament color: RHS NN155D (White). Anther shape: Oblong. Anther length: 0.25 mm. Anther color: RHS 195C (Greyed-green). Pollen amount: Low. Pollen color: RHS 161C (Greyed-yellow). Gynoecium: Present. Quantity of pistils per flower: Average 3, occasionally 2 or 4. Pistil length: 1.0 mm. Stigma shape: Club-shaped. Stigma color: RHS 157D (Green-white). Style length: 0.5 mm. Style color: RHS 157A (Green-white). Ovary color: RHS 145C (Yellow-green).

*Fertile flowers*.—Quantity of stamen per flower: Average 10. Filament length: 3.0 mm. Filament color: RHS NN155D (White). Anther shape: Oblong. Anther length: 0.4 mm. Anther color: RHS 155D (White). Pollen quantity: Low. Pollen color: RHS 161C (Greyed-yellow). Quantity of pistils per flower: Average 3, occasionally 2 or 4. Pistil length: 1.0 mm. Stigma shape: Club-shaped. Stigma color: RHS 157D (Green-white). Style length: 0.5 mm. Style color: RHS 157A (Green-white). Ovary color: RHS 145C (Yellow-green).

Seed: Not observed.

Disease and pest resistance: Similar to other varieties, no significant susceptibility for any disease.

COMPARISON WITH PARENTAL VARIETIES

Differences between the female parental line *Hydrangea paniculata* 'Grandiflora' and the 'OLLEDE' variety are described in Table 1 below.

TABLE 1

Comparison to Female Parent

| Characteristic | 'OLLEDE' | Female parent *Hydrangea paniculata* 'Grandiflora' |
|---|---|---|
| Length (Entire Plant) | Shorter | Taller |
| Flower Panicle | Compact | More open |
| Stem | Strong | Floppy |

COMPARISON TO KNOWN VARIETY

'OLLEDE' is most similar to the commercial *Hydrangea* plant named *Hydrangea paniculata* Little Spooky ('GRHPLS'), U.S. Plant Pat. No. 33,877. Differences between the two varieties are described in Table 2 below.

TABLE 2

Comparison with Similar Variety

| Characteristic | Variety 'OLLEDE' | Commercial line *Hydrangea paniculata* 'Little Spooky' |
|---|---|---|
| Flower | More compact than 'Little Spooky' | Less compact |
| Windmill flower leaves | More | Less |

I claim:

1. A new and distinct variety of *Hydrangea* plant named 'Ollede' as illustrated and described herein.

* * * * *